(12) United States Patent
Levit

(10) Patent No.: US 6,951,567 B2
(45) Date of Patent: Oct. 4, 2005

(54) TONGUE TREATING DEVICE

(76) Inventor: Bernardo Levit, Marcelo T. de Alvear 2345 PB "B", Ciudad de Buenos Aires (AR)

( * ) Notice: Subject to any disclaimer, the term of this patent is extended or adjusted under 35 U.S.C. 154(b) by 537 days.

(21) Appl. No.: 10/151,405

(22) Filed: May 17, 2002

(65) Prior Publication Data

US 2003/0216762 A1 Nov. 20, 2003

(51) Int. Cl.[7] .............................................. A61B 17/24
(52) U.S. Cl. ...................................................... 606/161
(58) Field of Search ................................ 606/161–160; D24/146; 144/115; 222/148, 149; 604/2, 3

(56) References Cited

U.S. PATENT DOCUMENTS

| | | |
|---|---|---|
| 619,466 A | 2/1899 | Buchmann |
| 1,033,819 A | 7/1912 | McMann |
| 1,498,267 A | 6/1924 | Hachman |
| 1,851,396 A | 3/1932 | Mabry |
| 1,983,601 A | 12/1934 | Conn |
| 2,218,072 A | 10/1940 | Runnels |
| 2,405,029 A | 7/1946 | Gallanty et al. |
| 2,543,999 A | 3/1951 | Voss |
| 2,560,746 A | 7/1951 | Scarkino |
| 2,583,750 A | 1/1952 | Runnels |
| 3,225,759 A | 12/1965 | Drapen et al. |
| 3,499,440 A | 3/1970 | Gibbs |
| 3,502,072 A | 3/1970 | Stillman |
| 3,509,874 A | 5/1970 | Stillman |
| 3,747,595 A | 7/1973 | Grossan |
| 3,890,964 A | 6/1975 | Castanedo |
| 3,943,628 A | 3/1976 | Kronman et al. |
| 3,973,558 A | 8/1976 | Stouffer et al. |
| 4,176,454 A | 12/1979 | Hatter et al. |
| 4,370,131 A | 1/1983 | Banko |
| 4,488,327 A | 12/1984 | Snider |
| 4,582,059 A | * 4/1986 | Tiwari ........................ 606/161 |
| 4,787,845 A | 11/1988 | Valentine |
| 4,958,751 A | 9/1990 | Curtis et al. |
| 4,973,250 A | 11/1990 | Milman |
| 4,979,504 A | 12/1990 | Mills |
| 5,127,831 A | 7/1992 | Bab |
| 5,217,475 A | 6/1993 | Kuber |
| 5,218,956 A | 6/1993 | Handler et al. |
| 5,220,914 A | 6/1993 | Thompson |
| 5,282,814 A | 2/1994 | Srivastava |
| 5,419,703 A | 5/1995 | Warrin et al. |
| 5,558,518 A | 9/1996 | Bab et al. |
| 5,567,153 A | 10/1996 | Foulkes et al. |
| 5,569,278 A | 10/1996 | Persad |
| 5,667,483 A | 9/1997 | Santos |
| 5,772,434 A | 6/1998 | Winston |
| 5,779,654 A | 7/1998 | Foley et al. |
| 5,817,114 A | * 10/1998 | Anderson et al. ........... 606/161 |
| 5,853,290 A | 12/1998 | Winston |
| 5,876,201 A | 3/1999 | Wilson et al. |
| 5,921,998 A | 7/1999 | Tano et al. |
| 5,947,912 A | 9/1999 | Montagnino |
| 5,980,541 A | 11/1999 | Tenzer |
| 5,980,542 A | 11/1999 | Saldivar |

FOREIGN PATENT DOCUMENTS

| | | |
|---|---|---|
| DE | 97517 | 8/1897 |
| DE | 296 18 012 | 4/1997 |
| FR | 468322 | 7/1914 |
| FR | 659404 | 6/1928 |

* cited by examiner

Primary Examiner—Julian W. Woo
(74) Attorney, Agent, or Firm—Greer, Burns & Crain, Ltd.

(57) ABSTRACT

A tongue scraping and treating device for use in removing undesired matter from a user's tongue and applying a substance on the tongue, the scraper comprising a curved scraper portion and handles connected to the scraper portion, wherein the scrapper portion includes a peripheral container channel at an upper edge thereof.

11 Claims, 2 Drawing Sheets

TONGUE TREATING DEVICE

BACKGROUND OF THE INVENTION

1. Field of the Invention

The present invention relates to a device for personal cleaning and, more particularly, to a scraper device for removing undesired matter from a user's tongue and, even more particularly, the invention relates to a scraper and tongue-treating device for removing plaque and debris from the tongue in order to prevent halitosis and for applying a treating substance onto the tongue.

2. Description of the Prior Art

Halitosis is a concern for many people affected of this disorder that is chronic or pathological disorder stemming from non-oral sources as well as oral sources. Studies have shown that about 85% patients suffering from halitosis have an oral condition as the source. Measures of oral malodor suggest that it is caused mainly by tongue coating as the result of anaerobic sulfur producing bacteria, which normally live within the tongue. This bacteria is supposed to be there because they assist digestion by breaking down proteins found in specific foods, mucus, blood and death cells. Under certain conditions, they start to break down the proteins found in those specific foods.

Tongue coating comprises desquamated epithelial cells, blood cells, bacteria and mucus. The morphology of the dorsal surface of the tongue is very irregular with the presence of multiple fissures and filiform and fungiform papillae. These fissures and crypts may create a unique ecological site were microorganisms are well-protected from the flushing action of the saliva and where oxygen levels are low enhancing the growth of anaerobic bacteria. Saliva from nearby glands drips down on the posterior region of the tongue, which is full of irregularities. The bacteria on the tongue are also a potential contributor to periodontal disease and other oral health problems. This coating on the tongue also causes a loss of taste since it dulls the taste receptors.

The anaerobic bacteria break down specific components of the coating of the tongue creating certain gases or volatile sulfur compounds (VSCs). These VSCs have been implicated as a major contributing factor to halitosis. Consequently, the removal of the tongue coating reduces VSCs production and longer lasting reductions in VSC levels are followed after tongue scraping. Methods that involved cleansing of the dorsoposterior surface of the tongue caused the most pronounced reductions of halitosis.

Many instruments have been developed and manufactured for removing debris and plaque from the tongue, these instruments comprising a tongue cleaning with a scraping portion having a blade designed to be passed onto the upper surface of the tongue to scrape the matter.

U.S. Pat. No. 5,827,308 to Thakur et al. discloses a tongue scraping apparatus having a curved blade and a pair of elongated handles, the blade including a relatively sharp lower edge, an opposed smooth upper edge, and opposed front and back faces. When using this apparatus in cleaning the upper surface of a tongue, the matter scraping from the tongue of a user is accumulated against the front face reaching the upper edge and passing in some cases over the upper edge to fall, by the back face, onto the surface of the tongue what is a very disgusting situation.

U.S. Pat. No. 6,013,089 to Goldberg discloses an improved tongue cleaner having a U-shaped scraper portion and handle portions integrally formed, with the scraper portion having a flange projected perpendicularly from an inner face of the scraper portion. The flange forms a corner space or a barrier in the inner face for containing matter scraped from the user's tongue.

While Goldberg has addressed the problem of the matter passing over the upper edge of the scraping blade, the provision of a simple flange does not solve the problem as it would be desired. In addition, the scrapers of Goldberg and Thakur lack any means for containing and applying a substance, such as a gel, onto the tongue's surface for treating purposes.

SUMMARY OF THE INVENTION

It is therefore one object of the present invention to provide an improved device for scraping the tongue of a user for removing matter, debris and/or plaque from the tongue in order to prevent mouth odor.

It is still another object of the present invention to provide a tongue scraping device capable of containing and applying a desired substance on the surface of the tongue with the purpose of treating or deodorizing the tongue.

It is a further object of the present invention to provide a tongue scraping device having a scraper portion with a lower scraping edge having a contour matching the anatomical shape of the tongue in order to improve the scraping.

It is even another object of the present invention to provide a tongue scraper for use in removing undesired matter from a user's tongue, the scraper comprising a curved scraper portion having an inner face, an outer face, a lower edge, and an opposed upper edge, and handle means connected to respective ends of the scraper portion, wherein the lower edge defines a contour comprising a central pending curved portion and two side concave curved portions placed at both sides of the central portion, the lower edge with the three curved portions matching an upper surface of the tongue, and wherein the outer surface includes a peripheral container channel at the upper edge, the channel provided either for collecting the matter scraped from the tongue and/or for containing a substance for treating the tongue.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
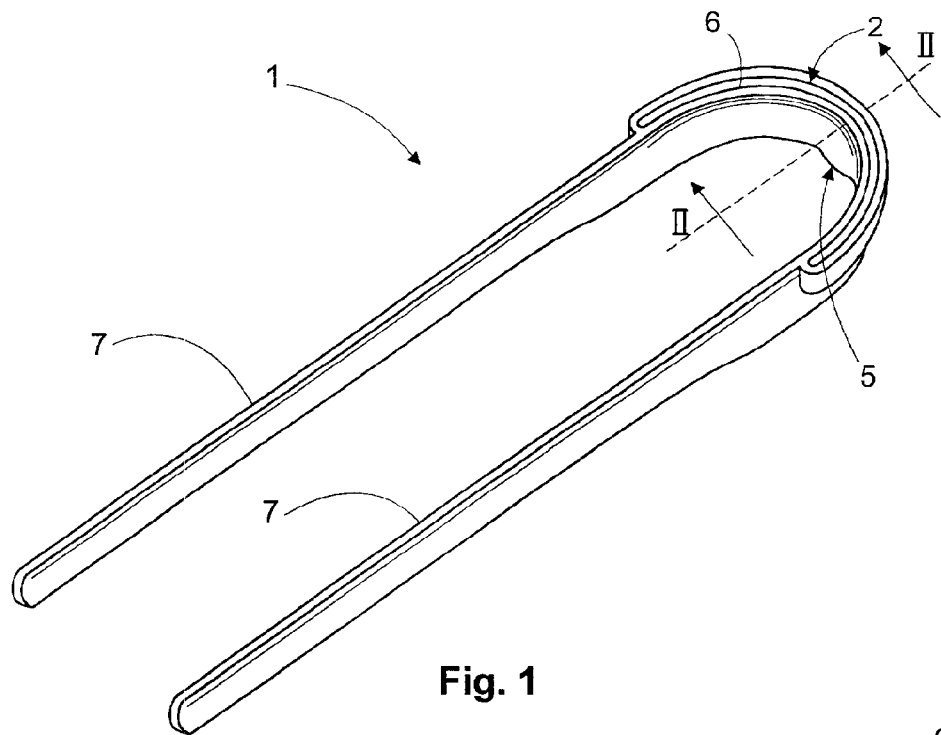
FIG. 1 shows a top perspective view of a scraper device according to the invention.
Figure 2:
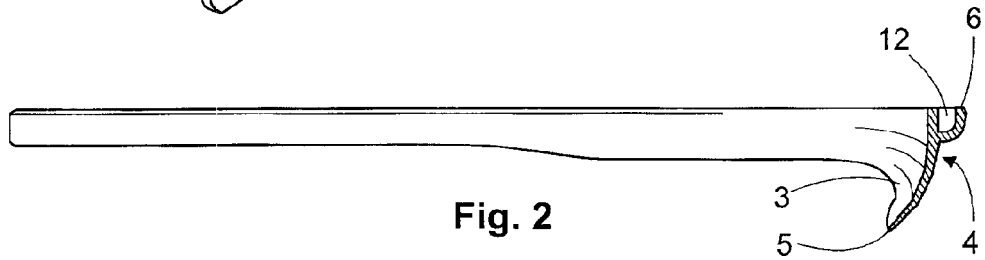
FIG. 2 shows a cross-sectional view taken along line II—II of FIG. 1.

Now referring in detail to the drawings it may be seen from FIGS. 1 and 2 that a scraper device according to an embodiment of the invention comprises tongue scraper 1 for use in removing undesired matter from a user's tongue and/or for applying a desired substance, such as a gel for refreshing the tongue. Scraper 1 comprises a curved scraper portion 2 having an inner face 3, an outer face 4, a lower edge 5, and an opposed upper edge 6. Scraper portion 1 is preferably a U-shaped flexible portion, made of any bioacceptable material, plastics, resins and the like, that is appropriate to be accommodated onto the upper surface of the tongue. Handle means comprising a pair of handles are connected to respective ends of scraper portion 1, wherein scraper portion 1 and handles 7 are integral and made of the same flexible material.

Figure 3:
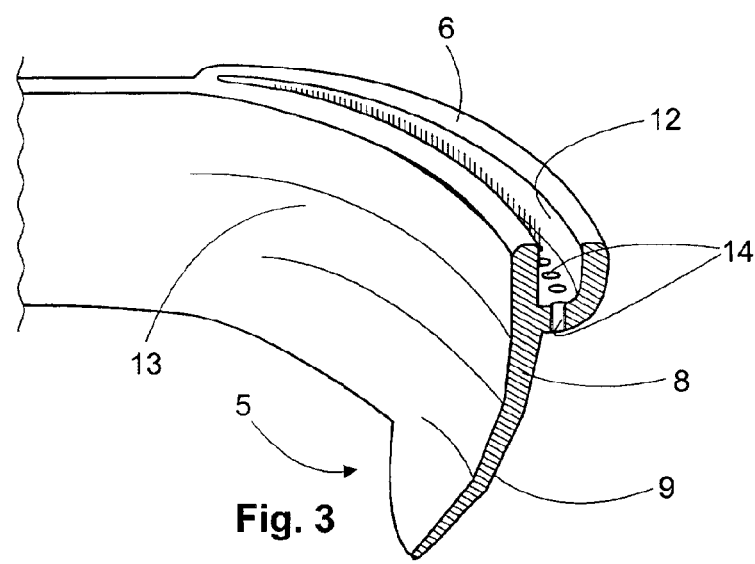
FIG. 3 shows a partial cross-sectional view of the scraper portion and container channel of the device of the invention, with the channel including orifices for controllably releasing a gel for deodorizing the tongue.

The curved scraper portion has a cross sectional shape, as better shown in FIGS. 2 and 3, comprising an upper portion 8 and a lower portion 9 angularly pending from the upper portion and ending in a relatively sharp configuration for lower edge 5. More precisely, curved scraper portion 2 has a cross sectional shape, better shown in FIG. 3, comprising a plurality of rectilinear portions angularly pending relative to each other. Each rectilinear portion preferably comprises a truncated cone shaped cross section or trapezoidal cross section except the bottom portion including edge 5, which bottom portion is a triangular-shaped round-ended portion. In addition, the rectilinear portions may have the same or different lengths.

Figure 4:
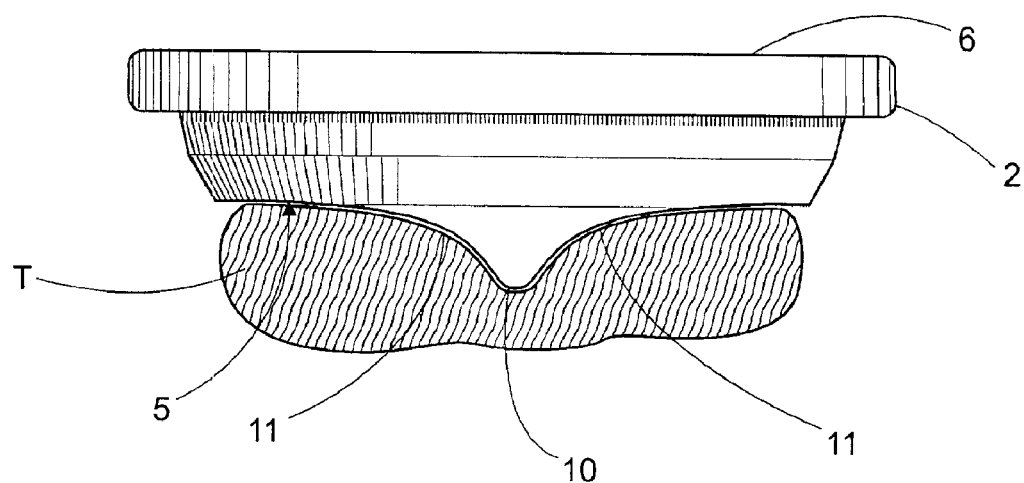
FIG. 4 shows a front elevation view of the scraper portion of the device of FIG. 1.
Figure 5:
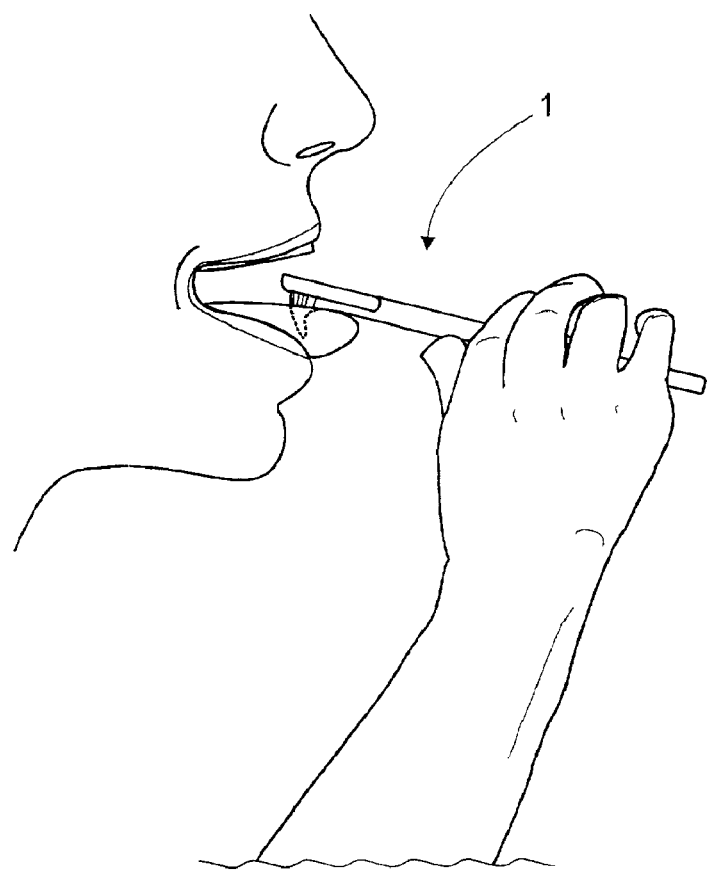
FIG. 5 shows a side schematic view of the device of the invention in operation.

Lower edge 5 defines a contour, better illustrated in FIG. 4, comprising a central pending curved portion 10 and two side pending concave portions 11, with portions 11 being placed at both sides of central portion 10. This configuration of the lower edge, namely the three curved portions 11, 10, 11, has the purpose of matching an anatomical shape of the tongue T, and more particularly the upper surface of the tongue and the median lingual sulcus to obtain an improved scraping and scanning action of this surface.

According to another feature of the invention, the device is provided with the capability of containing any desired matter or substance with the purpose of applying the same on the user's tongue. More particularly, outer surface 4 includes a peripheral container channel 12 at upper edge 6 of the scrapping portion. The peripheral container channel is formed by a curved wall 13 outwardly and upwardly extending from outer surface 4 in order to form a cavity all along the U-shaped scraper portion for at least two purposes. One purpose is to collect all the scraped matter collected against inner wall 3 that may reach the upper edge of wall 13 and pass over edge 6. Thus, unlike the US Patent to Goldberg, the scraped matter passing over edge 6 will fall into channel 12 and be collected therein. For this purpose, channel 12 preferably will have no orifices or openings at the bottom thereof.

Another purpose of channel 12 is to contain a substance, preferably a gel, in an appropriate manner to dispense the substance on the tongue for treating purposes. This gel may be for deodorizing purposes. Curved wall 13 preferably extends upwardly up to a level with upper edge 6, however, wall 13 may end below the level of upper edge 6 or above this level according to a preferred design. In all cases, upper edge 6 and the upper edge of wall 13 define respective smooth surfaces.

According to a preferred design, container channel 12 extends upwardly through a vertical extension of the outer surface that is about the 0.25 of the entire height of outer face 4, that is ¼ of a distance between upper edge 6 and lower edge 5.

For the purpose of controllably releasing a substance contained in channel 12, the peripheral container channel includes at least one opening, preferably a plurality of orifices 14, at a bottom thereof for controllably releasing the gel. Preferably, a continuous opening, not shown, will be provided at the bottom of channel 12.

Also for the purpose of containing and releasing a substance on the tongue, channel 12 may be like it is illustrated in FIGS. 1 and 2, that is without orifices 14. In this event, after using or not the device in a scraping operation, peripheral channel 12 may be filled with the substance, a gel for example, and the device may be placed upside down, that is with channel in an inverted position and oriented towards the upper surface of the tongue. Immediately, the device may be passed over the tongue as if it would be operating in a scraping position, thus pouring and releasing the gel along the tongue.

As an alternative embodiment channel 12 may contain a disposable spongy member, which in turn may contain the above-mentioned substance, such as a gel, in order to provide a controlled release of the substance onto the tongue. The spongy member may be any piece of sponge, porous material or absorbent member made of any appropriate material, such as a plastic foam, capable of retaining and releasing the substance.

While preferred embodiments of the present invention have been illustrated and described, it will be obvious to those skilled in the art that various changes and modifications may be made therein without departing from the scope of the invention as defined in the appended claims.

I claim:

1. A tongue scraper for use in removing undesired matter from a user's tongue, the scraper comprising:

a curved scraper portion comprising a plurality of rectilinear portions angularly pending relative to each other, the curved scraper portion having an inner face, an outer face, a lower edge, and an opposed upper edge, and handle means connected to respective ends of the scraper portion, wherein the lower edge defines a contour comprising a central pending curved portion and two side concave curved portions placed at both sides of the central portion, the lower edge with the three curved portions matching an upper surface of the tongue, and wherein the outer face includes a peripheral container channel at the upper edge.

2. The tongue scraper of claim 1, wherein the scraper portion is a U-shaped flexible portion.

3. The tongue scraper of claim 2, wherein the handle means comprise two handles, each handle being connected to a respective end of the U-shaped portion.

4. The tongue scraper of claim 3, wherein the scraper portion and the handles are integral and made of a flexible material.

5. The tongue scraper of claim 1, wherein the lower edge, with the three curved portions anatomically matching an upper surface of the tongue, is relatively sharp for improving the scraping action.

6. The tongue scraper of claim 5, wherein the curved scraper portion has a cross sectional shape comprising a plurality of rectilinear portions angularly pending relative to each other.

7. The tongue scraper of claim 1, wherein the peripheral container channel is formed by a curved wall outwardly and upwardly extending from the outer face for containing a substance for treating the tongue.

8. The tongue scraper of claim 7, wherein the curved wall extends upwardly to a level with the upper edge.

9. The tongue scraper of claim 7, wherein the peripheral container channel includes at least one opening at a bottom thereof for controllably releasing the substance.

10. The tongue scraper of claim 7, wherein the container channel extends upwardly through a vertical extension of the outer face that is about the 0.25 of a distance between the upper edge and the lower edge.

11. The tongue scraper of claim 1, wherein the upper edge has a smooth surface.

* * * * *